（12）United States Patent
Li (10) Patent No.: US 10,667,724 B2
(45) Date of Patent: Jun. 2, 2020

(54) SYSTEM AND METHOD FOR CONTINUOUS BACKGROUND HEARTRATE AND HEARTBEAT EVENTS DETECTION USING A MOTION SENSOR

(71) Applicant: Samsung Electronics Co., Ltd., Suwon-si, Gyeonggi-do (KR)

(72) Inventor: Yelei Li, Santa Clara, CA (US)

(73) Assignee: Samsung Electronics Co., Ltd. (KR)

( * ) Notice: Subject to any disclaimer, the term of this patent is extended or adjusted under 35 U.S.C. 154(b) by 120 days.

(21) Appl. No.: 15/726,827

(22) Filed: Oct. 6, 2017

(65) Prior Publication Data

US 2019/0046077 A1 Feb. 14, 2019

Related U.S. Application Data

(60) Provisional application No. 62/543,260, filed on Aug. 9, 2017.

(51) Int. Cl.
*A61B 5/11* (2006.01)
*A61B 5/00* (2006.01)
*A61B 5/0205* (2006.01)
*A61B 5/024* (2006.01)

(52) U.S. Cl.
CPC .......... *A61B 5/1102* (2013.01); *A61B 5/1118* (2013.01); *A61B 5/681* (2013.01); *A61B 5/0022* (2013.01); *A61B 5/0205* (2013.01); *A61B 5/02405* (2013.01); *A61B 5/742* (2013.01)

(58) Field of Classification Search
CPC ..... A61B 5/1102; A61B 5/0022; A61B 5/681; A61B 5/0205
See application file for complete search history.

(56) References Cited

U.S. PATENT DOCUMENTS

| | | | |
|---|---|---|---|
| 2009/0149779 A1* | 6/2009 | Russo | A61B 5/02405 600/595 |
| 2011/0066042 A1* | 3/2011 | Pandia | A61B 5/029 600/484 |
| 2014/0073486 A1* | 3/2014 | Ahmed | A61B 5/02405 482/9 |
| 2017/0273635 A1* | 9/2017 | Li | A61B 5/7278 |

* cited by examiner

*Primary Examiner* — Joseph M Dietrich
(74) *Attorney, Agent, or Firm* — McAndrews, Held & Malloy, Ltd.

(57) ABSTRACT

As a non-limiting example, various aspects of this disclosure provide embodiments of continuous background heartrate and heartbeat events detection using a motion sensor during various phases of activity by a user.

22 Claims, 9 Drawing Sheets

SYSTEM AND METHOD FOR CONTINUOUS BACKGROUND HEARTRATE AND HEARTBEAT EVENTS DETECTION USING A MOTION SENSOR

RELATED APPLICATIONS

This application claims the benefit of the U.S. Provisional Application 62/543,260, filed on Aug. 9, 2017, the disclosure of which is incorporated herein in its entirety by reference. The U.S. application Ser. No. 15/726,756 filed on even date herewith, titled "System and Method for Real-Time Heart Beat Events Detection Using Low-Power Motion Sensor" and which claims the benefit of the U.S. Provisional Application 62/543,270, filed on Aug. 9, 2017, is incorporated herein in its entirety by reference. The U.S. application Ser. No. 14/928,072 is incorporated in its entirety by reference. The U.S. application Ser. No. 15/264,333 is incorporated herein in its entirety by reference. The U.S. application Ser. No. 15/168,531 is incorporated herein in its entirety by reference.

BACKGROUND

Certain embodiments of the disclosure relate to biometric equipment and more specifically to a system and method for continuous background heartrate and heartbeat events detection using a motion sensor.

Limitations and disadvantages of conventional and traditional approaches will become apparent to one of skill in the art through comparison of such systems with some aspects of the present disclosure as set forth in the remainder of the present application with reference to the drawings.

SUMMARY

The present disclosure discloses a system and method for continuous background heartrate and heartbeat events detection using a motion sensor, substantially as shown in and/or described below, for example in connection with at least one of the figures, as set forth more completely in the claims.

These and other advantages, aspects and novel features of the present disclosure, as well as details of an illustrated embodiment thereof, will be more fully understood from the following description and drawings.

BRIEF DESCRIPTION OF THE DRAWINGS

These and/or other aspects will become apparent and more readily appreciated from the following description of the exemplary embodiments, taken in conjunction with the accompanying drawings.

DETAILED DESCRIPTION

Various example embodiments of the disclosure will be described in detail with reference to the accompanying drawings such that they can be made and used by those skilled in the art.

Various aspects of the present disclosure may be embodied in many different forms and should not be construed as being limited to the example embodiments set forth herein. Rather, these example embodiments of the disclosure are provided so that this disclosure will be thorough and complete and will convey various aspects of the disclosure to those skilled in the art.

The terminology used here is for the purpose of describing particular embodiments only and is not intended to limit the disclosure. In the drawings, the thickness, width, length, size, etc., of layers, areas, regions, components, elements, etc., may be exaggerated for clarity. Like reference numerals refer to like elements throughout.

As utilized herein, "and/or" means any one or more of the items in the list joined by "and/or." As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y, and/or z" means "one or more of x, y, and z". As utilized herein, the term "exemplary" means serving as a non-limiting example, instance, or illustration. As utilized herein, the terms "e.g." and "for example" set off lists of one or more non-limiting examples, instances, or illustrations.

Also, the singular forms are intended to include the plural forms as well, unless the context clearly indicates otherwise. It will be further understood that the terms "comprises," "comprising," "includes," and/or "including," when used in this specification, specify the presence of stated features, numbers, steps, operations, elements, and/or components, but do not preclude the presence or addition of one or more other features, numbers, steps, operations, elements, components, and/or groups thereof.

In addition, it will be understood that when an element A is referred to as being "connected to" or "coupled to" an element B, the element A can be directly connected to or coupled to the element B, or an intervening element C may be present between the elements A and B so that the element A can be indirectly connected to or coupled to the element B.

Furthermore, although the terms first, second, etc., may be used to describe various members, elements, regions, layers and/or sections, these members, elements, regions, layers and/or sections should not be limited by these terms. These terms are only used to distinguish one member, element, region, layer, and/or section from another. Thus, for example, a first member, a first element, a first region, a first layer, and/or a first section discussed below could be termed a second member, a second element, a second region, a second layer, and/or a second section without departing from the teachings of the present disclosure.

Spatially relative terms, such as "upper," "lower," "side," and the like, may be used for ease of description to describe the relationship of one element or feature to another element(s) or feature(s) as illustrated in the figures. It will be understood that the spatially relative terms are intended to encompass different orientations of the device in use or operation in addition to the orientation depicted in the figures. For example, if the device in the figures is turned upside-down, elements described as "below" or "beneath" other elements or features would then be oriented "above" the other elements or features. Thus, the term "below" can encompass both an orientation of above and below.

Furthermore, a term such as a "module," "block," etc., may comprise hardware and/or software components, and may further comprise other modules/blocks/etc., as well as be a part of a larger module or a block. Generally, the terms "module" and "block" may be interchangeable. "Software" may be used as a generic term for any code executable by a hardware device, and, hence, may include other similar terms such as, for example, firmware.

The detailed description set forth below is intended as a description of various example embodiments of a system and method for real-time heartbeat events detection using a low-power motion sensor. Usage of low-power motion sensor for real-time heartbeat events detection may be described in more detail in the U.S. application Ser. No. 15/168,531 filed on Mar. 28, 2016, titled "Method and Apparatus for Heart Rate and Respiration Rate Estimation Using Low Power Sensor."

The description is not intended to represent the only forms in which the present disclosure may be constructed or utilized. The description sets forth the features of the present disclosure in connection with the illustrated embodiments. It is to be understood, however, that the same or equivalent functions and structures may be accomplished by different embodiments that are also intended to be encompassed within the spirit and scope of the invention. As denoted elsewhere herein, like element numbers are intended to indicate like elements or features.

According to various embodiments, the present system for detecting heartbeat events may use a motion sensor to provide a signal, and various techniques such as, for example, combined channel selection, cross-correlation, a probability hybrid network, etc., may operate on the signal. In this disclosure, a smart scheduling framework for continuous heartrate and heartbeat events detection using a motion sensor is detailed. A low-power, low-noise motion sensor, which may be a part of, for example, a wrist-worn device such as the user-wearable device 100 described with respect to FIG. 1, configured to detect heartbeat events may increase the battery life of the user-wearable device 100. Additionally, the precision of the beat locations may be increased compared to other embodiments for detecting heartbeats.

The present disclosure includes a system and method for providing heartrate (HR) and heartbeat detection using a motion sensor. The system and method includes a HR monitoring framework for a dual-mode monitoring system. In a normal mode, the system may utilize the motion sensor to provide resting HR and heartbeat events information. Activity level information from motion sensor may be used to switch the operation mode. For example, when a user's activity level as measured by the motion detector exceeds a threshold, the system may switch from a normal mode to a low-power mode. In the low-power mode, the motion detector is utilized to provide heartrate detection. This framework may be used, for example, to replace optical sensor based HR monitoring.

Heart rate and heartbeat are conventionally detected using an electrocardiogram (ECG) or photoplethysmogram (PPG). An ECG utilizes electrical activity and requires multiple leads positioned at different points on the body. A PPG takes optical measurements of light absorption using a pulse oximeter. For wearable applications, placing multiple electrodes on the body is impractical. Similarly, using PPG is also not ideal for wearable applications since it has relatively high power requirements. Ballistocardiography (BCG), which may also be referred to as seismocardiography (SCG), among other terms, involves the measurement of ballistic forces on the heart. In wearable applications, it may be possible to take BCG measurements using the accelerometer of a wearable device. However, these types of measurements may be affected by movements of the user wearing the device. For example, the wearable device may be placed on a user's wrist, which may be prone to sudden and unexpected motion.

While this disclosure uses the term BCG for ease of description, it should be understood that BCG generally refers to measurement of heart functions using the movement of the body indicative of those functions. Accordingly, various other terms that describe similar functions as BCG, such as, for example, seismocardiography (SCG), are understood to be encompassed by the term BCG.

The descriptions set forth below are intended as a description of example embodiments of systems and methods for continuous background heartrate and heartbeat event detection using a motion sensor, and are provided in accordance with the present disclosure, and are not intended to represent the only forms in which the present disclosure may be constructed or utilized. The description sets forth the features of the present disclosure in connection with the illustrated embodiments. It is to be understood, however, that the same or equivalent functions and structures may be accomplished by different embodiments that are also intended to be encompassed within the spirit and scope of the invention. As denoted elsewhere herein, like element numbers are intended to indicate like elements or features.

According to various embodiments, the present system includes a framework for motion sensor-based heart rate and heartbeat event detection on a wearable device. In this disclosure, among other things, a smart scheduling framework for continuous heartrate and heartbeat events detection using a motion sensor is detailed.

Figure 1:
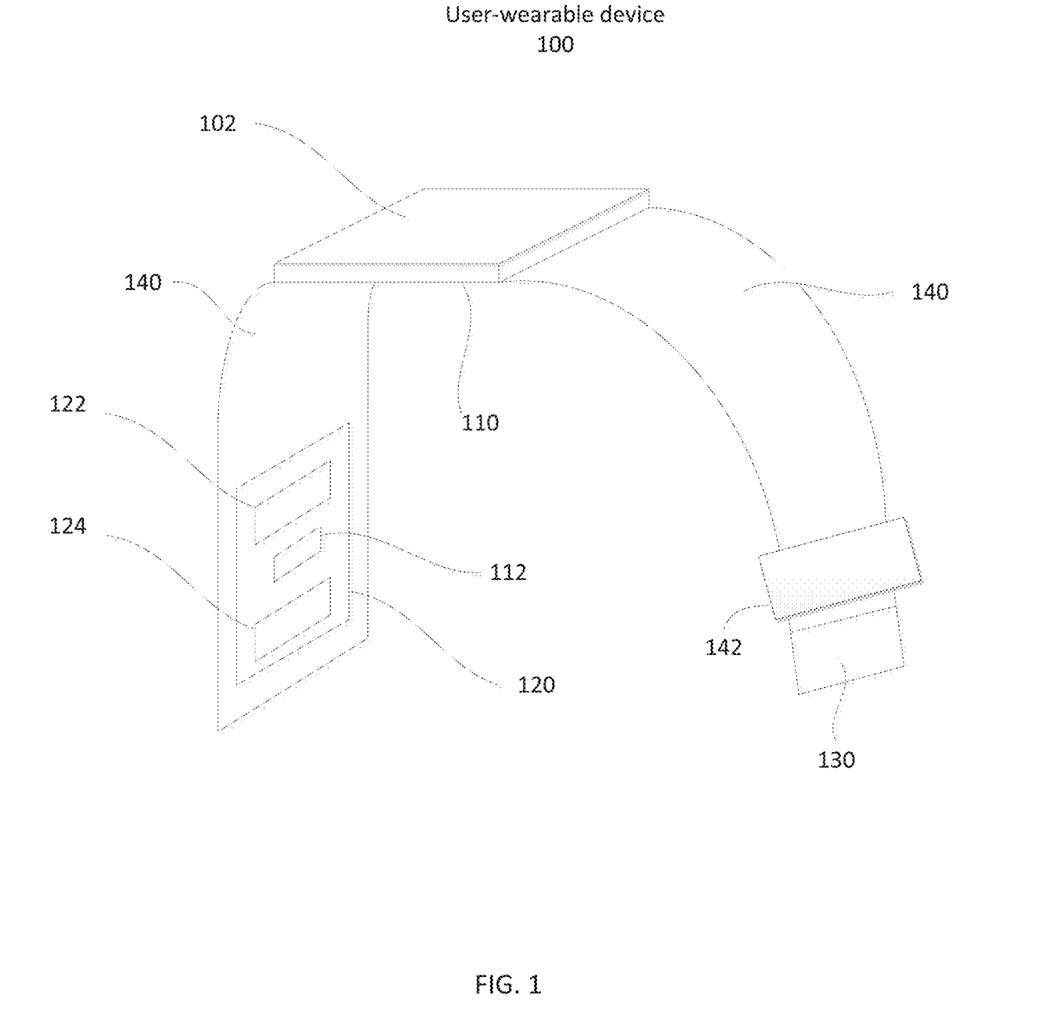
FIG. 1 is a diagram illustrating an electronic device, in accordance with various example aspects of this disclosure.

FIG. 1 is a diagram illustrating an electronic device in accordance with an embodiment of the present disclosure. Referring to FIG. 1, an electronic device, such as the user-wearable device 100, has a display 102, control block 110, the processor 112, a sensor module 120, a battery 130, a band 140, and a clasp 142. The sensor module 120 may include sensors 122 and 124. The control block 110, the processor 200 (FIG. 2), and/or the processor 112 may also be referred to as a diagnostic processor, and may be able to execute instructions. Accordingly, a diagnostic processor may comprise, for example, a digital signal processor, a controller, a use specific processor, a general processor, and so on. At times, for ease of description, a diagnostic processor may also generally refer to a combination of various hardware.

Although the user-wearable device 100 can be worn on a wrist, various embodiments of the disclosure need not be so limited. The user-wearable device 100 may also be designed to be worn on other parts of the body, such as, for example, on an arm (around the forearm, the elbow, or the upper arm), on a leg, on the chest, on the head like a headband, on the throat like a "choker," and on an ear. The user-wearable device 100 may be able to communicate with other electronic devices such as, for example, a smartphone, a laptop, or various medical devices at a hospital or a doctor's office. This will be described in more detail with respect to FIG. 3.

The display 102 may output monitored physiological signals from the user's body for viewing by the user and/or others. The signals being monitored may be referred to as biosignals or biometric data. The monitored signals may be, for example, heart (pulse) rate, pulse morphology (shape), pulse spacing (inter-beat intervals), respiration (breathing) rate, and blood pressure. The display 102 may also output instructions to the user or others in the use of the user-wearable device 100 or use of other measurement devices, as well as status and diagnostic results, for example.

The control block 110 can receive the monitored signals via a sensor in the sensor module 120. The sensor module 120 may include, for example, the sensors 122 and 124 that may acquire signals from the user's wrist when the user-wearable device 100 is worn by a user, as well as provide other information that may indicate the user's body position, motion, and the like. The sensor 122 and/or the sensor 124 may comprise, for example, one or more of an accelerometer, a gyroscope, piezoelectric device, an optical sensor, a sensor using sonic frequencies, and the like. The processor 112 may control the sensors 122 and 124, and may also process the signals monitored by the sensors 122 and 124. Various embodiments of the disclosure may have the control block 110 also perform the functions of the processor 112. Various embodiments of the disclosure may also have different number of sensors.

The sensor 122 may be any suitable device that may be used to detect/monitor motion such as, for example, an accelerometer, a gyroscope, piezoelectric device, an optical sensor such as, for example, a camera, sonic sensor, and the like. Any of these devices that comprise the sensor 122 may use any technology suitable for implementation for the user-wearable device 100 The sensor 124 may be similar to the sensor 122 or a different type of sensor such as, for example, a thermometer for taking the user's temperature. Various embodiments of the disclosure may include different numbers of sensor modules. For example, some embodiments may only have one sensor module, while other embodiments may have two or more sensor modules.

The battery 130 is configured to provide power for the user-wearable device 100. The battery 130 may be charged using a wired charging system or a wireless charging system. The band 140 may be wrapped around a wrist and the user-wearable device 100 may be held on the wrist by using the clasp 142.

Figure 2:
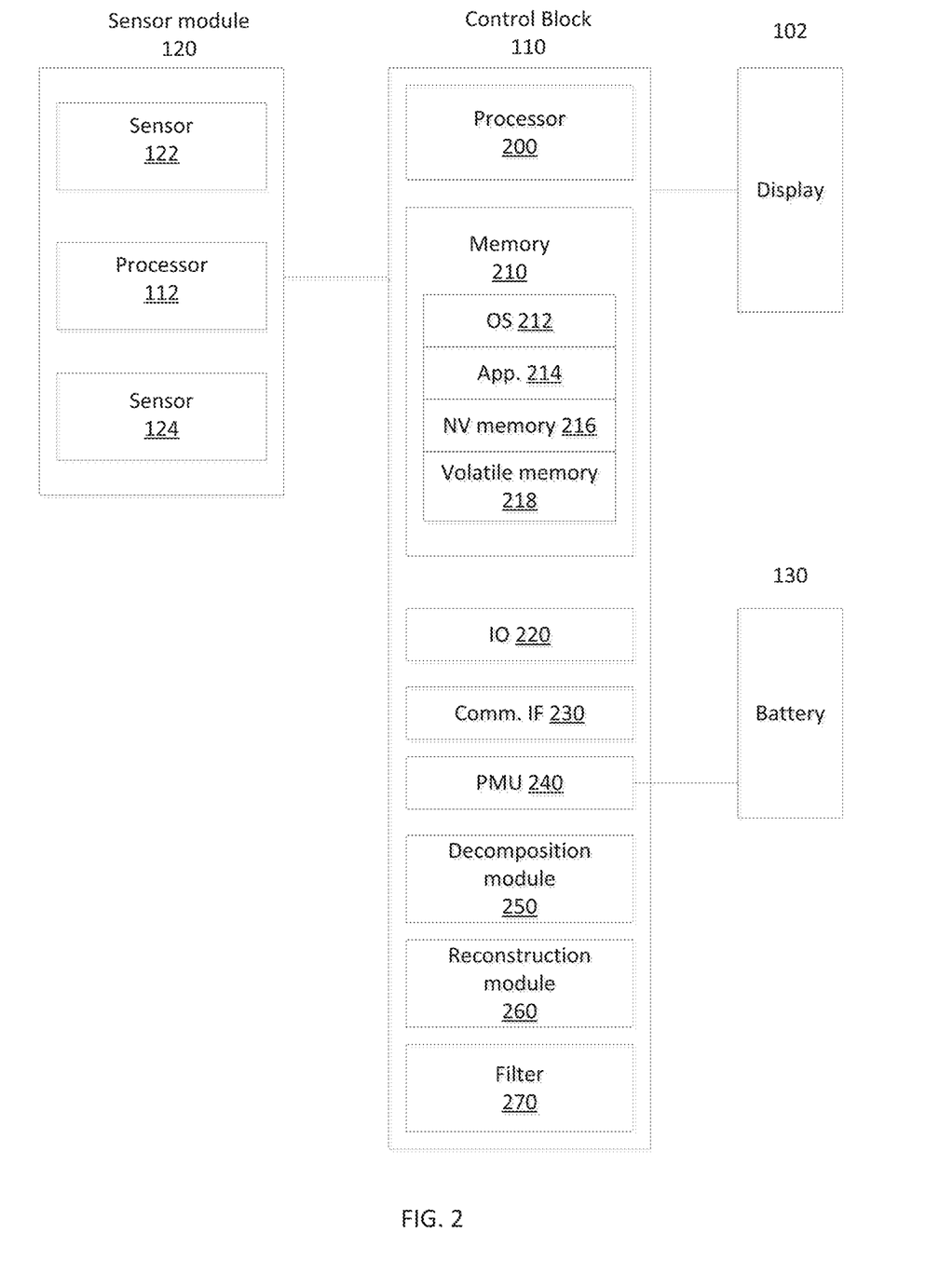
FIG. 2 is a high-level block diagram of an example electronic device, in accordance with various example aspects of this disclosure.

FIG. 2 is a high-level block diagram of an example electronic device in accordance with an embodiment of the present disclosure. Referring to FIG. 2, there is shown the display 102, the control block 110, the sensor module 120, and the battery 130. Output to the display 102 can be controlled, for example, by the control block 110. The display 102 may also include input devices (not shown) such as, for example, buttons, dials, touch sensitive screen, and microphone.

The control block 110 may include a processor 200, memory 210, an input/output (IO) interface 220, a communication interface 230, a power management unit (PMU) 240, a decomposition module 250, a reconstruction module 260, and a filter 270. While the control block 110 is described as including these various devices, other embodiments may use other architectures where the different functionalities are grouped differently. For example, the grouping may be in different integrated circuit chips. Or the grouping may be combining different devices such as the IO interface 220 and the communication interface 230 together, or the decomposition module 250 and the reconstruction module 260 together.

The processor 200 may control operation of the sensor module 120 as well as receive monitored signals from the sensor module 120. The processor 200 may control the user-wearable device 100, including processing the monitored signals from the sensor module 120, displaying the processed signals on the display 102, receiving input from the display 102, interfacing with various devices via the IO interface 220 or the communication interface 230 by executing instructions in the memory 210. The TO interface 220 may be used by the processor 200 to interface with the display 102.

The processor 112 may operate using different architectures in different embodiments. For example, the processor 112 may use the memory 210 to store instructions to execute, or the processor 112 may have its own memory (not shown) for its instructions. The processor 112 may also have other functionalities found in the control block 110. Although some embodiments have separate processors 200 and 112, the various embodiments need not be limited so. There may be one control block 110 that controls the functionality of the user-wearable device 100, or there may be multiple processors for the user-wearable device 100.

The memory 210 may include non-volatile memory 216 and volatile memory 218. The operating system and applications may be stored in the non-volatile memory 216. Various embodiments of the disclosure may use different memory architectures that are design and or implementation dependent.

The communication interface 230 may allow the user-wearable device 100 to communicate with other devices via, for example, a wired or wireless protocol such as USB, Bluetooth, Near Field Communication (NFC), and WiFi. The PMU 240 may control receiving power from an outside source, charging the battery 130, as well as allocation of power to the different parts of the user-wearable device 100.

The decomposition module 250 may function to decompose, for example, an input signal such as a BCG signal to multiple frequency bands using time-frequency transforms. The reconstruction module 260 may function to reconstruct, for example, the decomposed signals from the decomposition module 250 to refine and access desired components of the original signal such as the BCG signal. Decomposition and reconstruction of a signal is explained in more detail in the U.S. application Ser. No. 14/928,072. The filter 270 may be used to attenuate specific frequencies from a signal. For example, the filter 270 may be a low-pass filter, high-pass filter, a bandpass filter, etc. The filter 270 may be a digital filter and/or an analog filter.

Figure 3:
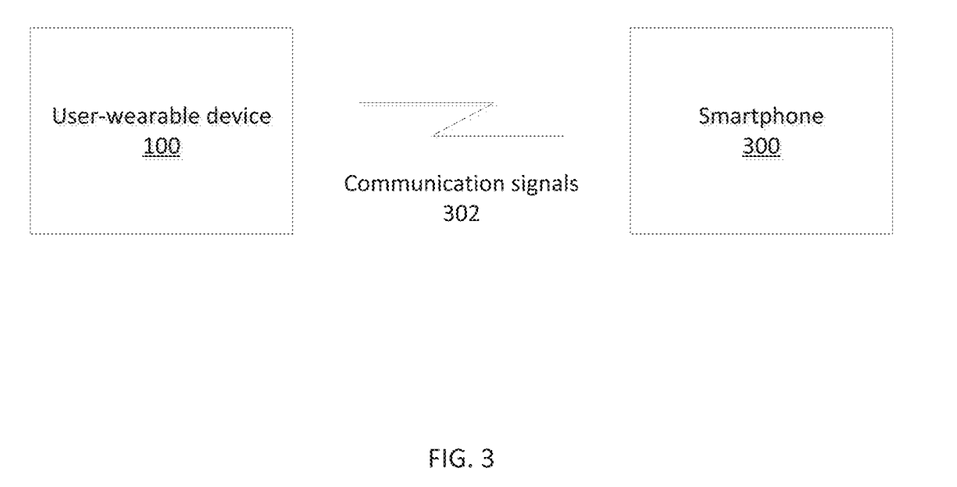
FIG. 3 is an illustration of an electronic device in a communication network, in accordance with various example aspects of this disclosure.
Figure 4A:
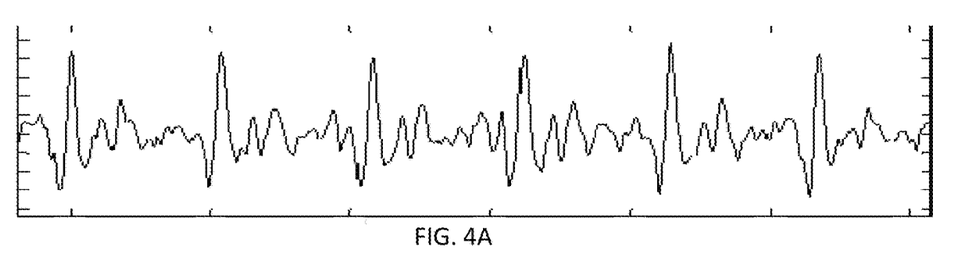
FIGS. 4A-4D illustrate example output waveforms of an accelerometer for different positions of an accelerometer at different periods of time, in conjunction with use of various example aspects of this disclosure.
Figure 4B:
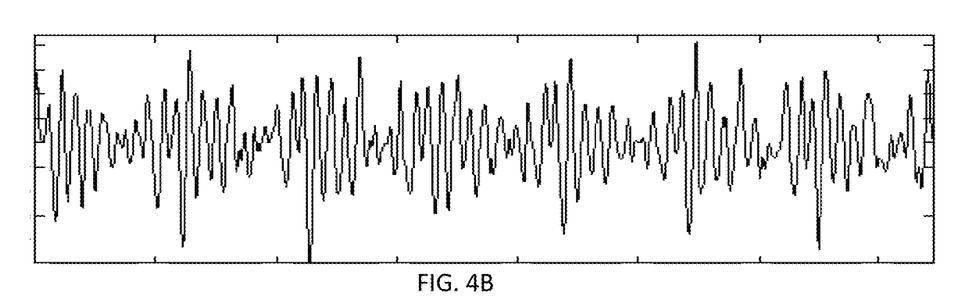
Figure 4C:
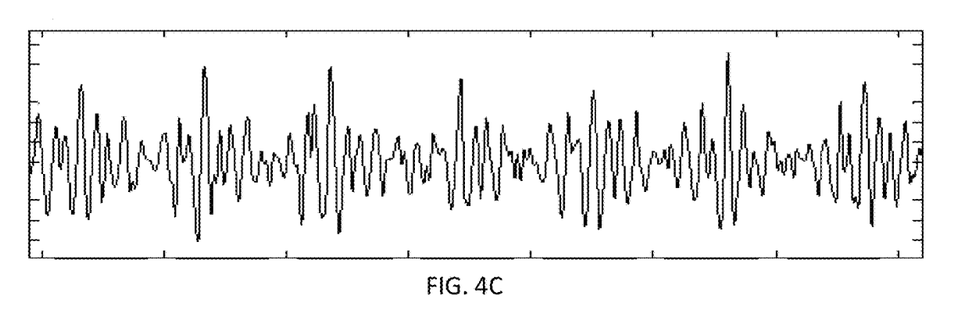
Figure 4D:
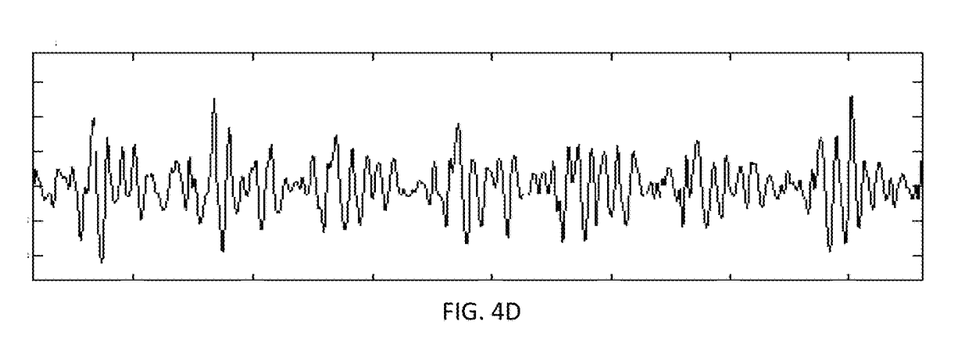

FIG. 3 is an illustration of an electronic device in a communication network in accordance with an embodiment of the present disclosure. Referring to FIG. 3, there is shown the user-wearable device 100 and a smartphone 300. The user-wearable device 100 may communicate with the smartphone 300 using the communication interface 230. The communication may be via the communication signals 302, where the communication may be direct between the user-wearable device 100 and a smartphone 300, or include other elements between the user-wearable device 100 and a smartphone 300.

One of the applications 214 of the user-wearable device 100 may allow the smartphone 300 to control at least some operation of the user-wearable device 100. For example, user-wearable device 100 may output to the display 102 a result of the processing by the control block 110, and/or the same result may be transmitted to the smartphone 300. Various embodiments may also allow other signals to be transmitted by the user-wearable device to one or more devices. For example, the user-wearable device 100 may transmit the raw sensor signal, or some form of the raw signals that has been processed to an external electronic device. The external device may be, for example, a medical device that may be able to perform more detailed processing and/or analysis than the user-wearable device. The user or another person may also select an option either on the user-wearable device 100 or on the external device such as, for example, the smartphone 300. The options may be, for example, to start a biosignal monitoring process by the user-wearable device 100 or to stop the biosignal monitoring process, which signals to transmit, etc.

Since the smartphone 300 has a larger display, it can be easier for the user to view a result or to select an option on the smartphone 300 rather than on the user-wearable device 100. However, it should be noted that the smartphone 300 may not generally be necessary for operation of the user-wearable device 100.

While a description was given of a smartphone 300, it should be noted that any suitable electronic device may be used. For example, the smartphone 300 may be replaced (or used in addition to) with a laptop, desktop, medical equipment used by health care providers, tablet, etc.

Heart rate and heartbeat are conventionally detected using an electrocardiogram (ECG) or photoplethysmogram (PPG). An ECG utilizes electrical activity and requires multiple leads positioned at different points on the body. A PPG takes optical measurements of light absorption using a pulse oximeter. Placing multiple electrodes on a user's body may be impractical for wearable applications such as, for example, the user-wearable device 100. Similarly, PPG may also be problematic for wearable devices such as the user-wearable device 100 due to its relatively high power requirements.

Ballistocardiography (BCG) measures body acceleration caused by cardiac output as well as respiration. BCG contains multiple peak events during one heartbeat. These peaks can be categorized into three major groups: pre-systolic, systolic, and diastolic. Systolic waves may correspond to QRS complexes in ECG signal, and they may be a salient features of BCG. BCG signals, however, may also include a wide variety of peaks due to frequency position (orientation) changes as well as level of stability of the measured subject.

In wearable applications, it may be possible to take BCG measurements using, for example, an accelerometer of the user-wearable device 100. However, it may be useful to take into account the movements of the user wearing the user-wearable device 100 as these movements may act as noise to the BCG measurements. This may be especially true if the user-wearable device 100 is worn on a user's wrist, which may be prone to sudden and unexpected motions.

Accordingly, various embodiments of the disclosure may describe a system for detecting heartbeat events using a motion sensor using one or more of combined channel selection, cross-correlation, and a probability hybrid network. By using a low-power, low-noise motion sensor to detect heartbeat events, the battery life of the device may be significantly extended. Additionally, the precision of the beat locations may be increased.

Various embodiments described below may require less power compared to, for example, an optical approach such as a PPG device, and yet provide precision when the user is active. When the user is stationary, the various embodiments may prove to be more flexible compared to an ECG device since the disclosed algorithm(s) may enable heartbeat event detection at various body locations or even remote locations without having to have multiple leads positioned at different points of the user's body.

BCG waveforms may vary as the orientation of the motion sensor changes. For example, in one embodiment, the sensor module 120 in the user-wearable device 100 may comprise a sensor 122, which may be a motion sensor such as, for example, a 3-axis accelerometer. BCG signals from the 3-axis accelerometer may vary whenever the orientation of the accelerometer changes. This can be seen in FIGS. 4A-4D, where an accelerometer outputs the example waveforms shown in FIGS. 4A-4D for different positions of the accelerometer.

Various embodiments of the disclosure may comprise hardware and software modules that operate to identify artifacts in the signals of a 3-axis accelerometer to generate a heartbeat signal. The artifacts may be caused by, for example, motion of the user-wearable device 100, muscle contraction of the body part that the user-wearable device 100 is on, etc.

Additionally, BCG channel fusion/selection may involve performing in real time data fusion for the signals output by the 3-axis accelerometer and/or switching to a different one of the three channels depending on which channel is determined to be the best candidate. Accordingly, various embodiments of the disclosure may provide heartbeat events by optimizing the output signals of the 3-axis accelerometer.

An embodiment may disclose a dual-mode system wearable-based system with a motion sensor. A normal mode of operation may occur when a user is relatively still, and a low-power mode of operation may occur when the user's motion exceeds a threshold. In one embodiment, the motion sensor may be an accelerometer such as, for example, a three-axis accelerometer.

Figure 5:
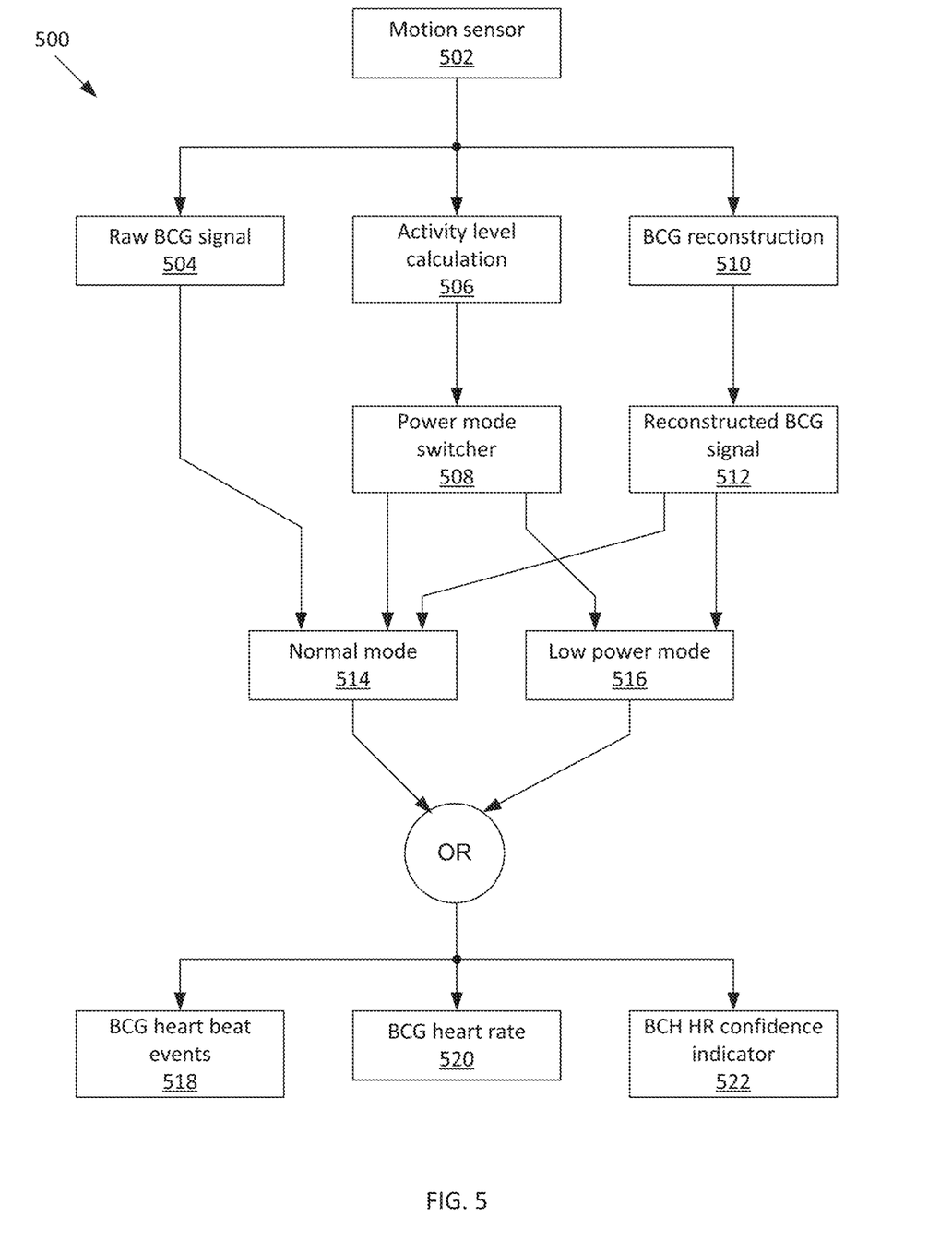
FIG. 5 is an example flow diagram for BCG background heart rate and heartbeat event detection, in accordance with various example aspects of this disclosure.

FIG. 5 is an example flow diagram for BCG background heart rate and heartbeat event detection, in accordance with various example aspects of this disclosure. Referring to FIG. 5, there is shown an example flow diagram 500 for a framework that includes a normal mode and a low-power mode. The determination of which mode the system is operating in may depend on the readings from the motion sensor. The motion sensor may be used to continuously monitor a subject's activity level. The motion sensor may include, for example, a 3-axis accelerometer.

At 502, a motion sensor, which may comprise, for example, a 3-axis accelerometer in the sensor 122 of the user-wearable device 100, may output raw motion data. At 504, the raw motion data may be provided for processing by the normal mode block at 514.

At 506, an activity level block may analyze the raw motion data to determine whether the level of activity is greater than an activity threshold. At 508, the output of the activity level block may be used by the power mode switcher block to determine whether the framework should be in normal mode or low-power mode. The power mode switcher block may put the system into normal mode when the subject is inactive or the activity level is below the activity threshold. The power mode switcher block may put the system into low-power mode when the subject is active or the activity level is above the activity threshold.

In some embodiments, a sleep onset/offset flag may be used as a trigger to switch between the normal mode and the low-power mode. For example, determining that a user is asleep may trigger the switch to a normal mode, and determining that a user is awake may trigger the switch to a low-power mode. In another example, time information may additionally be used to enhance accuracy of mode switch. For example, there may typically be less activity late at night than in the middle of the day, and a greater likelihood that low activity level indicates that the user is sleeping.

In a generalized framework, a power mode switch flag may be triggered according to activity level. However, a triggering threshold may be varied for different use cases. For example, when the framework is implemented into wrist band such as, for example, the user-wearable device 100, a low threshold may be expected since even a subtle wrist movement may degrade BCG signal quality. In another use case when the framework is implemented into a device that attaches to a body part such as the abdomen, chest, or ear, a high threshold may be set since the BCG signal may be relatively strong and there may not be as much body movement.

At 510, the raw motion data may be provided to the BCG reconstruction block. The BCG reconstruction block may reconstruct using, for example, the reconstruction module 260, the decomposed signals from the decomposition module 250 to refine and access desired components of the original signal. Decomposition and reconstruction of a signal is explained in more detail in the U.S. application Ser. No. 14/928,072. The BCG reconstruction block is described as comprising the decomposing and reconstruction functions for the sake of expedience in this disclosure.

At 512, the reconstructed BCG signal may be provided for further processing by the normal mode block at 514 and the low-power mode block at 516.

At 514, the system may be in a normal mode because the user may be in a low-activity level state such as when sleeping or being in a prolonged resting state with minimal motion. In normal mode, heart rate and heartbeat event information may be generated from one or both of the reconstructed signal and the raw motion data. Various embodiments may also generate a heart rate confidence indicator. Heartbeat event information may be used to calculate biometrics such as, for example, heart rate variability (HRV), stress, cardiac arrhythmia detection, blood pressure calculation, etc. The various functions of the normal mode block may be explained in more detail by the U.S. application Ser. Nos. 14/928,072, 15/264,333, and 15/168,531.

At 516, the system may be in a low-power mode because the user may be awake and/or active, and continuous heart rate (HR) and a HR confidence indicator may be provided. In an embodiment, the motion sensor may be used to monitor the user's activity continuously in the background and trigger a heartrate (HR) calculation when a stationary period is detected. In one embodiment, when the framework is implemented into, for example, a user-wearable device 100 such as a wrist band, the HR algorithm may be triggered when the wrist is mostly stationary for a predetermined time period (e.g. 5 seconds). Some embodiments may store the signals during the 5 second period so that the heart rate may be provided for those 5 seconds, as well.

Based on requirements of downstream algorithms, the report resolution may be further adjusted. This may allow a smart schedule mechanism to optimize continuous heart rate monitoring duty cycle and provide flexible resolution for different use cases.

At 518, the heartbeat events may be provided for downstream applications; at 520, the heart rate may be provided for downstream applications; and at 522, a HR confidence indicator may be provided for downstream applications.

One or more of the outputs of the system at 518, 520, and/or 522 may be provided, for example, to be displayed on the display 102 if the system is part of the user-wearable device 100. One or more of the outputs may also be transmitted by a transmitter to another electronic device as described in FIG. 3.

BCG signal quality in low-power mode may be worse than in normal mode due to body movements, muscle contraction, and other artifacts. Accordingly, enhanced signal quality may be desired, as well as being able to identify and exclude invalid segments of the BCG signal.

Each of the functionality in FIG. 5 may be performed by hardware circuitry and/or one or more processors executing software instructions.

Figure 6:
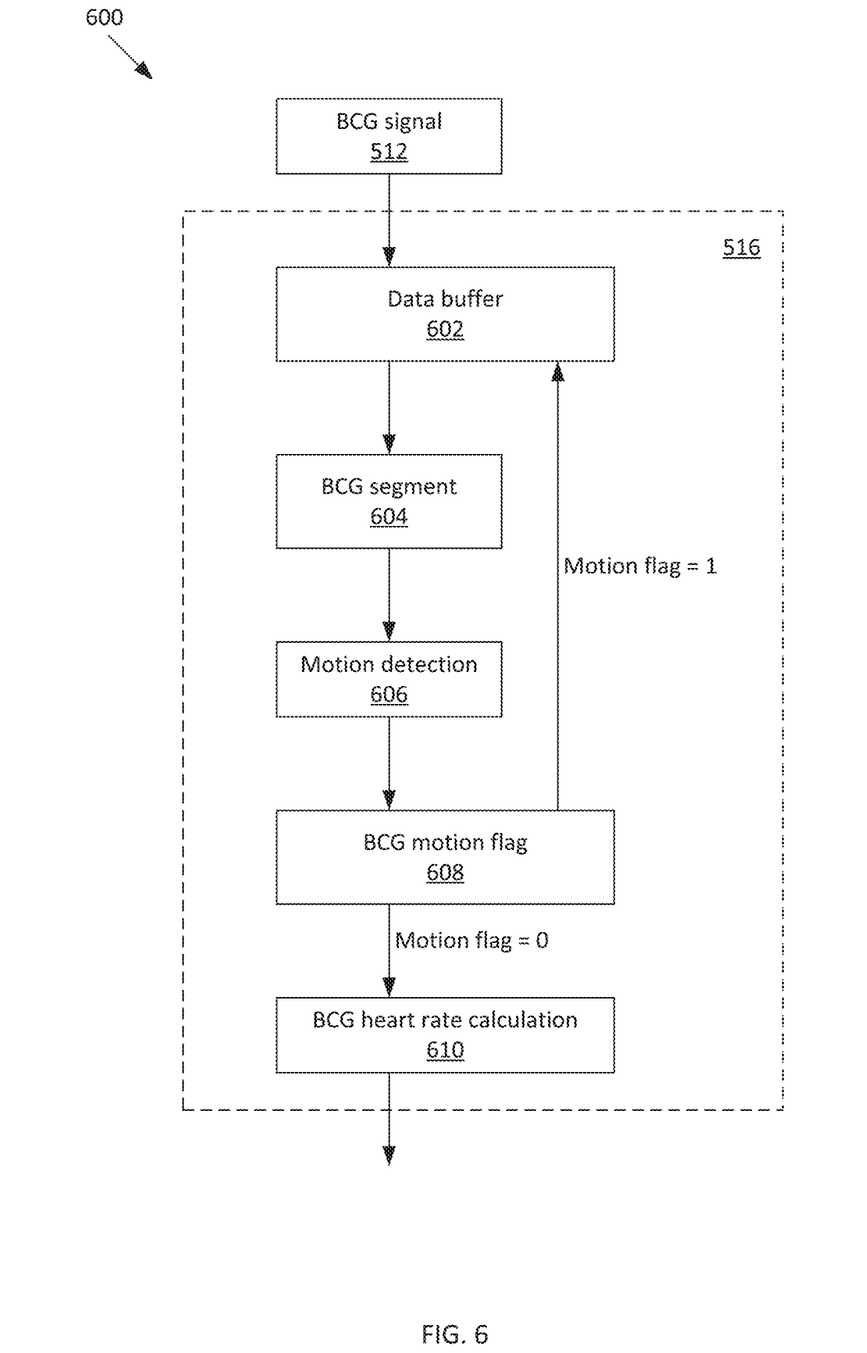
FIG. 6 is an example flow diagram for the BCG motion detection triage block, in accordance with various example aspects of this disclosure.

FIG. 6 is an example flow diagram for the BCG motion detection triage block, in accordance with various example aspects of this disclosure. Referring to FIG. 6, there is shown the flow diagram 600. At 602, the reconstructed BCG signal may be sampled by a sampling circuit configured to convert an analog signal to a digital signal, and the samples may be stored in the data buffer 602.

If, for example, the HR algorithm is triggered after a 5 second stationary period, a buffer may be allocated to store samples for 5 seconds of the reconstructed BCG signal. Accordingly, if the sample rate is 100 samples per second, then the buffer may be large enough to store 500 samples. The samples may be stored in the buffer in a looping basis where the beginning of the buffer is overwritten with new data when the end of the buffer is reached. The buffer may be allocated from, for example, the memory 210. Other methods, such as, for example, using two or more buffers, may also be appropriate. Various other techniques such as, for example, interrupts, may also be used for keeping track of a period of time with little activity.

The HR calculation may continue with the stored data until the activity level rises above a threshold. The data buffer(s) may then be reset to flush the data. Other embodiments may stop storing data when the activity level rises above the threshold so that the HR may be calculated for as much data as is stored. When all of the data has been processed to determine the HR, the stored data may be flushed. Accordingly, the HR may be able to be determined whenever there is a brief period of low activity by processing the stored data. Other embodiments may not start HR calculation until the activity level has been determined to be low for a required period of time such as, for example, 5 seconds.

Two thresholds may be used in an embodiment of the disclosure. The first threshold may be directly applied to a 5-second BCG segment at 604 where a sample point value is set to 1 if its amplitude is above the first threshold. These samples with a value of 1 may be referred to as motion samples. Otherwise, the sample point value is set to 0. These samples with a value of 0 may be referred to as non-motion samples. Motion ratio, which may be defined as, for example, the percentage of sample point values with a value of 1, or motion samples, compared to the total number of samples (motion samples plus non-motion samples) may be calculated at 606. These processes may be performed by, for example, a processor such as the processor 112 or 200.

At 608, the motion ratio may be compared with a second threshold, and a motion flag may be set to 1 if the motion ratio is greater than a second threshold, otherwise, the motion flag may be set to 0. If the motion flag is 1 to indicate unacceptable activity level, then the next set of data from the data buffer may be used at 602. If the motion flag is 0 to indicate acceptable activity level, then BCG heart rate calculation may be performed at 610.

The two thresholds may be predetermined, and may be changed depending on the design and/or implementation of the system. As an example, one or both of the thresholds may be dependent on, for example, the motion ratio over a period of time.

Each of the functionality in FIG. 6 may be performed by hardware circuitry and/or one or more processors executing software instructions.

Figure 7:
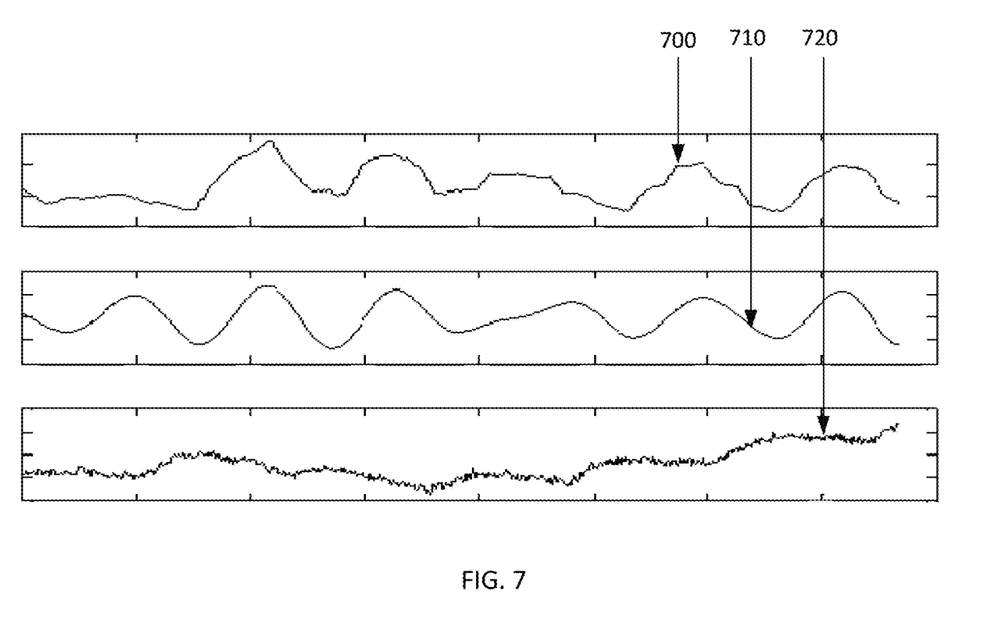
FIG. 7 illustrates an example of BCG pre-processing, in accordance with various example aspects of this disclosure.

FIG. 7 illustrates an example of BCG pre-processing, in accordance with various example aspects of this disclosure. Referring to FIG. 7, there is shown a signal trace 700 for a raw BCG segment and a signal trace 710 that is a pre-processed version of the signal trace 700. For comparison, there is also shown a PPG signal trace 720 in FIG. 7.

According to various embodiments, pre-processing may be provided at various times during processing an input motion sensor signal. For example, the pre-processing may occur to a raw signal and/or to a reconstructed signal. The pre-processing may enhance the BCG signal quality. One method of pre-processing may be to apply filtering using, for example, a bandpass filter or a high pass filter to remove dominating baseline wandering. The filtering may be done, for example, to the BCG signal before it is sampled and stored in the data buffer.

Time frequency approach may also be used to expand signal characteristics in both domains and extract valuable information. In one embodiment, a pre-processing block may perform discrete wavelet decomposition and reconstruction to separate the BCG signal into desired frequency bands and then combine selected bands as desired. Discrete wavelet decomposition and reconstruction may be explained in more detail in the U.S. application Ser. No. 15/168,531.

Feature extraction approaches such as principle component analysis (PCA), factor analysis, etc., may also be used. In one embodiment, denoising autoencoder may be used to reduce BCG nonlinear dimensionality. A fully trained denoising autoencoder in this case may be considered as a nonlinear PCA. Other machine learning approaches such as, for example, convolutional network may also be used for pre-processing.

BCG heart rate calculation may use one or more of different methodologies. For example, for a single BCG segment, a fast Fourier transform (FFT) of the segment may be directly calculated and dominate frequency peaks may be identified as heart rate candidates. In one example, a BCG segment may be set to a 5 second period with 100 Hz sampling rate, and a zero padding operation may be applied to the original BCG segment in order to increase frequency resolution. An interpolation operation may also be used on the frequency plot to further increase resolution.

A time domain beat detection based approach may also be suitable to identify heartbeat events and further calculate heart rate. There may be various options to implement time domain HR analysis. For example, in one embodiment, an adaptive threshold may be applied on the BCG segment, and the highest peak of each crossing section may be considered as one heartbeat. In another embodiment, time-delay embedding (TDE) based beat detection approach may be applied. TDE based approach may be explained in more detail in the U.S. application Ser. No. 15/264,333.

Heart rate calculation also can be achieved using other options. For example, a recurrence plot may be applied to identify periodicity of given segment.

Additionally, because BCG quality may not be very good during the low-power mode, multiple heart rate calculation blocks may be used, and the results may be processed to output a single heart rate value as well as heart rate confidence indicator.

A probability calculation block may also be used, where a probability block may indicate the confidence level of BCG heart rate candidates. The quantification may include signal quality measurement, correlation between multiple HR candidates, retrained probability model, etc.

Various embodiments may use a first method where frequency analysis result and time domain analysis result may be compared. If the absolute difference between the values is less than 3 beat per minute (BPM), heart rate confidence indicator may be set to '1' and the average HR may be output as the HR. Otherwise the HR confidence indicator may be set to '0'.

Various embodiments may use a second method where frequency analysis may be applied on multiple pre-processed BCG signal (e.g. IIR filtered signal, wavelet filtered signal, etc.). Each segment may produce a different frequency plot due to the difference of filtering characteristics. Accordingly, the HR may be determined by comparing and/or combining the different frequency plots, and the HR confidence indicator may be set accordingly.

Additionally, a hybrid network may be used that combines the first and second methods described above, as well as other suitable methods. A hybrid network is described with respect to FIG. 8.

Figure 8:
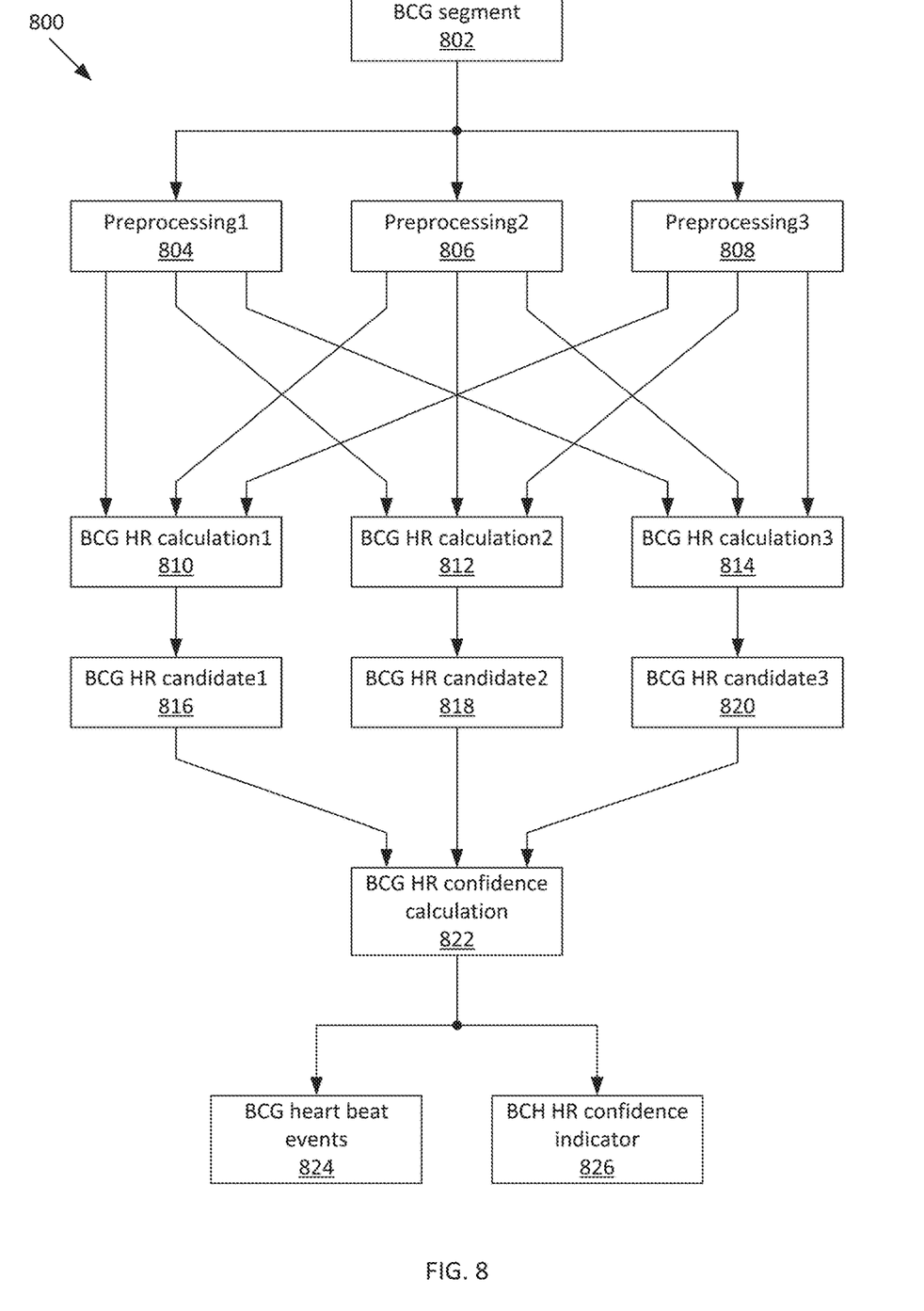
FIG. 8 is an example of a hybrid network for pre-processing, in accordance with various example aspects of this disclosure.

FIG. 8 is an example of a hybrid network for pre-processing, in accordance with various example aspects of this disclosure. Referring to FIG. 8, there is shown a flow diagram 800. At 802, a BCG segment may be output for pre-processing at 804, 806, and 808. Each pre-processing block may perform a pre-processing operation at 804, 806, and 808. The pre-processing blocks may each perform pre-processing that may be different from each other, whether in the processing or in use of parameters that may affect the same process. Each of the pre-processing blocks may output the pre-processed signals to the various HR calculation blocks.

Accordingly, each of the pre-processing operations at 804, 806, and 808 may comprise one or more methods such as, for example, filtering the BCG signal before it is sampled and stored in the data buffer to remove dominating baseline wandering, performing discrete wavelet decomposition and reconstruction to separate the BCG signal into desired frequency bands and then combine selected bands as desired, etc. Pre-processing may also comprise feature extraction approaches such as principle component analysis (PCA), factor analysis, etc., where denoising autoencoder may be used to reduce BCG nonlinear dimensionality, and a fully trained denoising autoencoder may be considered as a nonlinear PCA. Other machine learning approaches such as, for example, convolutional network may also be used for pre-processing.

The BCG signal pre-processed at 804 may be provided for HR calculation at 810, 812, and 814. Similarly, the BCG signal pre-processed at 806 may also be provided for HR calculation at 810, 812, and 814, and the BCG signal pre-processed at 808 may be provided for HR calculation at 810, 812, and 814.

At 816, the pre-processed BCG signals may be compared and/or combined in a first way to generate a first HR candidate. Similarly, at 818, the pre-processed BCG signals may be compared and/or combined in a second way to generate a second HR candidate, and, at 820, the pre-processed BCG signals may be compared and/or combined in a third way to generate a third HR candidate.

At 822, the first HR candidate, the second HR candidate, and the third HR candidate may be analyzed by the HR confidence calculation block with respect to each other to determine the HR confidence level at 826. The HR confidence calculation block may also generate an output heart rate and/or heartbeat events from the various HR candidates at 824. For example, if the HR candidates are all within a certain range with respect to each other (e.g., within 3 beats of each other), then the HR confidence indicator may be set to a '1'. Otherwise, the HR confidence indicator may be set to a '0'.

Various embodiments may have the HR confidence indicator set to more values than just the binary '0' and '1' according to design and/or implementation decisions. For example, a probability block may be used to give confidence probability.

While FIG. 8 was shown as having three independent pre-processing blocks, various embodiments of the disclosure need not be so limited. There may be two pre-processing blocks, or more than three pre-processing blocks. Additionally, determining the confidence calculation indicator from the various HR candidates may depend on design and/or implementation. For example, the HR candidates may be averaged, or outlier HR candidate may be thrown out, etc.

The pre-processing, the HR calculation, the HR confidence calculation, the BCG heartbeat events generation, and the HR confidence indicator generation may be performed by hardware circuitry and/or one or more processors executing software instructions.

Figure 9:
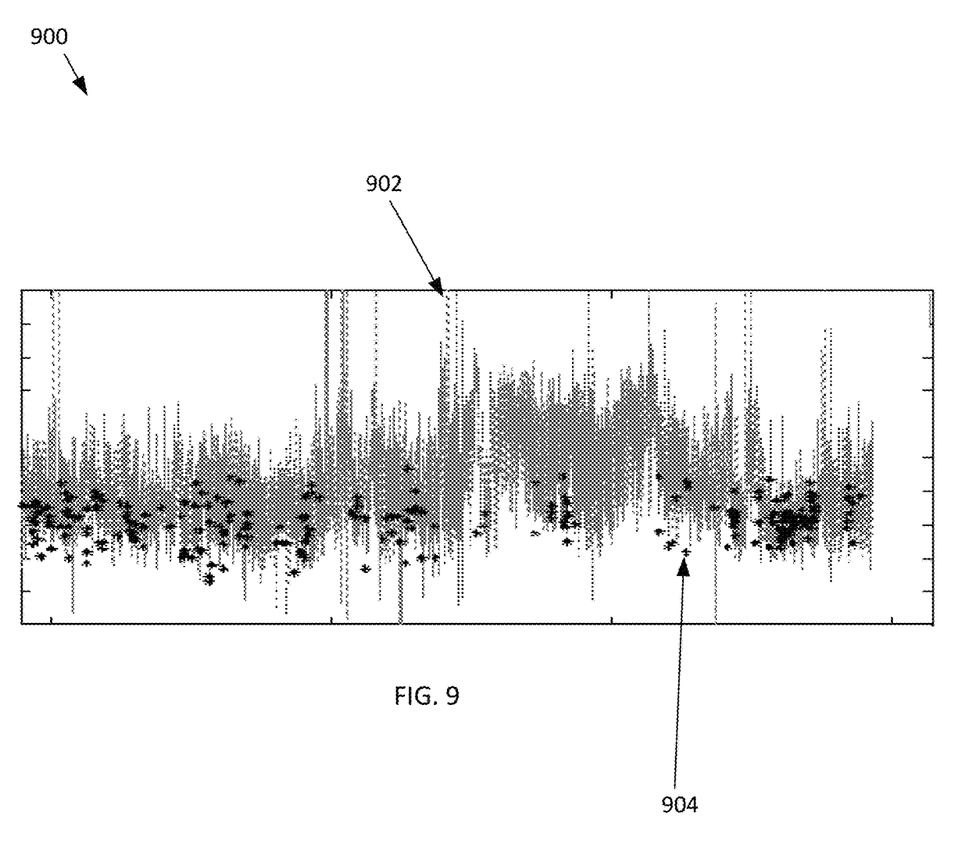
FIG. 9 is an illustration of an example BCG low power mode heart rate trend with reference comparison, in conjunction with use of various example aspects of this disclosure.

FIG. 9 is an illustration of an example BCG low power mode heart rate trend with reference comparison, in conjunction with use of various example aspects of this disclosure. Referring to FIG. 9, there is shown the heart rate chart 900 that has the reference heart rate 902 from an ECG measurement and the low power mode heart rate 904. The X-axis may be time, and the Y-axis may be the heart rate.

The frameworks described may comprise hardware modules and/or software modules for performing various calculations and functions. The various blocks described with respect to FIGS. 5-8 may comprise hardware and/or software modules and may be found, for example, in the sensor module 120 and/or the control block 110. The software modules may comprise instructions that may be executed, for example, by the processor 112 and/or the processor 200, or other processors that may be used by, for example, the user-wearable device 100. The hardware module may include various types of circuitry that may be used for a specific functionality. For example, the circuitry may be in a custom designed IC (including ASIC, FPGA, etc.) or an off-the-shelf part suitable for the functionality.

Various embodiments of the disclosure may include an electronic device configured for use by a user, comprising a motion sensor configured to output a sensor signal that correlates to motion of the user, and an activity level block configured to receive the sensor signal to determine an activity level of the user based on the received sensor signal. The motion sensor may comprise at least one of an accelerometer, a gyroscope, piezoelectric device, an optical sensor, and a sonic sensor. A power mode switcher block may be configured to select, based on the activity level, either a first operation mode or a second operation mode. The first operation mode block may be configured to generate, when in the first operation mode, a continuous heart rate of the user and heartbeat event information. A second operation mode block may be configured to generate, when in the second operation mode, the continuous heart rate of the user and a heart rate confidence indicator.

The electronic device may comprise a filter configured to filter the received sensor signal to attenuate frequencies below a first frequency, where the filtered sensor signal may be provided to the first operation mode block and the second operation mode block. The electronic device, when operating in the second operation mode may consumes less power than operating in the first operation mode. The electronic device may be worn by the user, for example, on the wrist.

The electronic device may comprise a transmitter configured to transmit to another electronic device one or more of the sensor signal, the continuous heart rate, the heartbeat event information, and the heart rate confidence indicator.

The electronic device may comprise a pre-processing block configured to perform discrete wavelet decomposition and reconstruction on the sensor signal to generate a reconstructed signal. The reconstructed signal may be provided to the first operation mode block to generate, when in the first operation mode, the continuous heart rate of the user and the heartbeat event information, and provided to the second operation mode block to generate, when in the second operation mode, the continuous heart rate of the user and a heart rate confidence indicator.

One or both of the reconstructed signal and the sensor signal may be used during the first operation mode in generating one or both of the continuous heart rate of the user and the heartbeat event information. The reconstructed signal, but not the sensor signal, may be used during the second operation mode to generate one or both of the continuous heart rate of the user and the heart rate confidence indicator.

The electronic device may generate the heart rate confidence indicator by using a sampling circuit configured to generate samples of a segment of the reconstructed signal. A processor may be configured to identify motion samples, where the motion sample is a sample that has a magnitude greater than a first threshold. The processor may also be configured to determine a motion ratio, where the motion ratio is a percentage of the motion samples with respect to all the samples generated from the segment. The processor may then determine whether the motion ratio is greater than a second threshold, and set the heart rate confidence indicator to a '0' when the motion ratio is greater than the second threshold, and set the heart rate confidence indicator to a '1' when the motion ratio is less than or equal to the second threshold.

The electronic device may comprise multiple pre-processing modules in the pre-processing block, and may process in parallel the reconstructed signal to generate the continuous heart rate of the user and the heart rate confidence indicator. Each of the multiple pre-processing modules may generate a heart rate candidate, and process the heart rate candidates generated by the multiple pre-processing modules to generate one or both of the continuous heart rate of the user and the heart rate confidence indicator. Each of the multiple pre-processing modules may perform a unique pre-processing process on the reconstructed signal. The electronic device may comprise a display configured to display one or more of the continuous heart rate of the user, heartbeat event information, and the heart rate confidence indicator. The electronic device may comprise a transmitter configured to transmit one or more of the continuous heart rate of the user, heartbeat event information, and the heart rate confidence indicator.

Various embodiments of the disclosure may also include a method for an electronic device worn by a user, the method comprising receiving a sensor signal from a motion sensor and determining an activity level of the user based on the sensor signal. The method may comprise selecting, based on the activity level, one of a first operation mode and a second operation mode that consumes less power than the first operation mode, and generating when in the first operation mode, a continuous heart rate of the user and heartbeat event information, and when in the second operation mode, the continuous heart rate of the user and a heart rate confidence indicator.

The method may comprise filtering the received sensor signal to attenuate frequencies below a first frequency, where the filtered sensor signal may be provided to a first operation mode block and a second operation mode block.

The method may comprise performing discrete wavelet decomposition and reconstruction on the sensor signal to generate a reconstructed signal. The reconstructed signal may be provided for generating, when in the first operation mode, the continuous heart rate of the user and the heartbeat event information, and, when in the second operation mode, the continuous heart rate of the user and a heart rate confidence indicator.

One or both of the reconstructed signal and the sensor signal may be used during the first operation mode in generating one or both of the continuous heart rate of the user and the heartbeat event information. The reconstructed signal, but not the sensor signal, may be used during the second operation mode to generate one or both of the continuous heart rate of the user and the heart rate confidence indicator.

Generating the heart rate confidence indicator may comprise generating samples of a segment of the reconstructed signal and determining motion samples, where the motion sample is a sample that has a magnitude greater than a first threshold. A motion ratio may then be determined, where the motion ratio may be a percentage of the motion samples with respect to all the samples generated from the segment. Then it may be determined whether the motion ratio is greater than a second threshold. If so, then the heart rate confidence indicator may be set to a '0'. Otherwise, the heart rate confidence indicator may be set to a '1' when the motion ratio is less than or equal to the second threshold.

The method may comprise processing in parallel, by multiple pre-processing modules, the reconstructed signal to generate the continuous heart rate of the user and the heart rate confidence indicator, where each of the multiple pre-processing modules may perform a unique pre-processing process on the reconstructed signal.

The method may also comprise generating, by each of the multiple pre-processing modules, a heart rate candidate. The heart rate candidates generated by the multiple pre-processing modules may be processed to generate one or both of the continuous heart rate of the user and the heart rate confidence indicator.

One or more of the continuous heart rate of the user, heartbeat event information, and the heart rate confidence indicator may be provided to the display of the electronic device to be displayed. One or more of the continuous heart rate of the user, heartbeat event information, and the heart rate confidence indicator may also be transmitted to another electronic device.

Accordingly, various embodiments have been described for HR monitoring frameworks that provide resting HR and heartbeat events information. Activity level information from motion sensor may be used to switch operation mode between a normal mode when the activity level of the user is low and a low-power mode when the activity level of the user is high. The normal mode may also be referred to as a first operation mode, and the low-power mode may also be referred to as a second operation mode.

As compared to conventional background HR devices, there is power savings, there is no sensitivity to skin color, and there is no need to fit sensors to specific parts of the body.

Various embodiments of the disclosure use a smart scheduling framework to provide real-time applications for continuous heart rate and heartbeat events detection using a low-power motion sensor without latency and without warm up periods.

While various embodiments of the disclosure have been described above, it should be understood that they have been presented as non-limiting examples only. While the foregoing has been described with reference to certain aspects and examples, it will be understood by those skilled in the art that various changes may be made and equivalents may be substituted without departing from the scope of the disclosure. In addition, many modifications may be made to adapt a particular situation or material to the teachings of the disclosure without departing from its scope. Therefore, it is intended that the disclosure not be limited to the particular example(s) disclosed, but that the disclosure will include all examples falling within the scope of the appended claims.

What are claimed:

1. An electronic device for use by a user, comprising:
a motion sensor configured to output a sensor signal that correlates to motion detected from the user;
an activity level block configured to receive the sensor signal to determine an activity level of the user based on the received sensor signal;
a power mode switcher block configured to select, based on the activity level, one of a first operation mode and a second operation mode, wherein:
the first operation mode is selected when the activity level is below an activity threshold; and
the second operation mode is selected when the activity level is above the activity threshold;
a first operation mode block configured to generate, when in the first operation mode, a continuous heart rate of the user and heartbeat event information;
a second operation mode block configured to generate, when in the second operation mode, the continuous heart rate of the user and a heart rate confidence indicator; and
a pre-processing block configured to perform discrete wavelet decomposition and reconstruction on the sensor signal to generate a reconstructed signal,
wherein one or both of the reconstructed signal and the sensor signal is used during the first operation mode in generating one or both of the continuous heart rate of the user and the heartbeat event information.

2. The electronic device of claim 1, comprising a filter configured to filter the received sensor signal to attenuate frequencies below a first frequency, wherein the filtered sensor signal is provided to the first operation mode block and the second operation mode block.

3. The electronic device of claim 1, wherein the electronic device is worn by the user.

4. The electronic device of claim 1, comprising a transmitter configured to transmit to another electronic device one or more of the sensor signal, the continuous heart rate, the heartbeat event information, and the heart rate confidence indicator.

5. The electronic device of claim 1, wherein the motion sensor is one or more of an accelerometer, a gyroscope, piezoelectric device, an optical sensor, and a sonic sensor.

6. The electronic device of claim 1,
wherein the pre-processing block is configured to provide the reconstructed signal to:
the first operation mode block to generate, for use in the first operation mode, the continuous heart rate of the user and the heartbeat event information; and
the second operation mode block to generate, for use in the second operation mode, the continuous heart rate of the user and a heart rate confidence indicator.

7. The electronic device of claim 6, wherein generating the heart rate confidence indicator comprises:
a sampling circuit configured to generate samples from a segment of the reconstructed signal; and
a processor configured to:
identify motion samples, wherein the motion sample is a sample that has a magnitude greater than a first threshold;
determine a motion ratio, wherein the motion ratio is a percentage of the motion samples with respect to all the samples generated from the segment; and
determine whether the motion ratio is greater than a second threshold; and
perform one of:
setting the heart rate confidence indicator to a '0' when the motion ratio is greater than the second threshold; and
setting the heart rate confidence indicator to a '1' when the motion ratio is less than or equal to the second threshold.

8. The electronic device of claim 1, wherein the reconstructed signal, but not the sensor signal, is used during the second operation mode in generating one or both of the continuous heart rate of the user and the heart rate confidence indicator.

9. The electronic device of claim 1, wherein the pre-processing block comprises multiple pre-processing modules configured to process, in parallel, the reconstructed signal to generate the continuous heart rate of the user and the heart rate confidence indicator.

10. The electronic device of claim 9, wherein:
each of the multiple pre-processing modules is configured to generate a heart rate candidate; and
process the heart rate candidates generated by the multiple pre-processing modules to generate one or both of the continuous heart rate of the user and the heart rate confidence indicator.

11. The electronic device of claim 9, wherein each of the multiple pre-processing modules performs a unique pre-processing process on the reconstructed signal.

12. The electronic device of claim 1, comprising a display configured to display one or more of the continuous heart rate of the user, heartbeat event information, and the heart rate confidence indicator.

13. The electronic device of claim 1, comprising a transmitter configured to transmit one or more of the continuous heart rate of the user, heartbeat event information, and the heart rate confidence indicator.

14. A method for an electronic device worn by a user, comprising:
receiving a sensor signal from a motion sensor;
determining an activity level of the user based on the sensor signal;
selecting, based on the activity level, one of a first operation mode and a second operation mode that consumes less power than the first operation mode, wherein:
the first operation mode is selected when the activity level is below an activity threshold; and
the second operation mode is selected when the activity level is above the activity threshold;
generating:
when in the first operation mode, a continuous heart rate of the user and heartbeat event information; and
when in the second operation mode, the continuous heart rate of the user and a heart rate confidence indicator; and
performing discrete wavelet decomposition and reconstruction on the sensor signal to generate a reconstructed signal,
wherein one or both of the reconstructed signal and the sensor signal is used during the first operation mode in generating one or both of the continuous heart rate of the user and the heartbeat event information.

15. The method of claim 14, comprising filtering the received sensor signal to attenuate frequencies below a first frequency, wherein the filtered sensor signal is provided to a first operation mode block and a second operation mode block.

16. The method of claim 14, comprising
generating with the reconstructed signal:
when in the first operation mode, the continuous heart rate of the user and the heartbeat event information; and
when in the second operation mode, the continuous heart rate of the user and a heart rate confidence indicator.

17. The method of claim 14, wherein the reconstructed signal, but not the sensor signal, is used during the second operation mode to generate one or both of the continuous heart rate of the user and the heart rate confidence indicator.

18. The method of claim 14, wherein generating the heart rate confidence indicator comprises:
generating samples from a segment of the reconstructed signal;
determining motion samples, wherein the motion sample is a sample that has a magnitude greater than a first threshold;
determining a motion ratio, wherein the motion ratio is a percentage of the motion samples with respect to all the samples generated from the segment;
determining whether the motion ratio is greater than a second threshold; and
performing one of:
setting the heart rate confidence indicator to a '0' when the motion ratio is greater than the second threshold; and
setting the heart rate confidence indicator to a '1' when the motion ratio is less than or equal to the second threshold.

19. The method of claim 14, comprising processing in parallel, by multiple pre-processing modules, the reconstructed signal to generate the continuous heart rate of the user and the heart rate confidence indicator, wherein each of the multiple pre-processing modules performs a unique pre-processing process on the reconstructed signal.

20. The method of claim 19, comprising:
generating by each of the multiple pre-processing modules a heart rate candidate; and
processing the heart rate candidates generated by the multiple pre-processing modules to generate one or both of the continuous heart rate of the user and the heart rate confidence indicator.

21. The method of claim 14, comprising providing to a display of the electronic device for displaying, one or more of the continuous heart rate of the user, heartbeat event information, and the heart rate confidence indicator.

22. The method of claim 14, comprising transmitting to another electronic device one or more of the continuous heart rate of the user, heartbeat event information, and the heart rate confidence indicator.

* * * * *